United States Patent
Py

(10) Patent No.: US 12,097,984 B2
(45) Date of Patent: Sep. 24, 2024

(54) NEEDLE WITH CLOSURE AND METHOD

(71) Applicant: Dr. Py Institute, LLC, New Milford, CT (US)

(72) Inventor: Daniel Py, New Milford, CT (US)

(73) Assignee: Dr. Py Institute LLC, New Milford, CT (US)

( * ) Notice: Subject to any disclaimer, the term of this patent is extended or adjusted under 35 U.S.C. 154(b) by 108 days.

(21) Appl. No.: 17/508,812

(22) Filed: Oct. 22, 2021

(65) Prior Publication Data

US 2022/0219843 A1 Jul. 14, 2022

Related U.S. Application Data

(63) Continuation of application No. 13/450,306, filed on Apr. 18, 2012, now abandoned.

(60) Provisional application No. 61/476,523, filed on Apr. 18, 2011.

(51) Int. Cl.
| A61J 1/20 | (2006.01) |
| A61M 5/32 | (2006.01) |
| B65B 3/00 | (2006.01) |
| B65B 39/00 | (2006.01) |
| B65B 39/12 | (2006.01) |

(52) U.S. Cl.
CPC ............ *B65B 3/003* (2013.01); *A61J 1/2096* (2013.01); *A61M 5/32* (2013.01); *B65B 39/004* (2013.01); *B65B 39/12* (2013.01)

(58) Field of Classification Search
CPC ....... B65B 3/003; B65B 39/004; B65B 39/12; A61J 1/20; A61J 1/2096; A61M 5/31; A61M 5/32
See application file for complete search history.

(56) References Cited

U.S. PATENT DOCUMENTS

| 2,304,390 | A | | 12/1942 | Wolfram |
| 2,541,272 | A | * | 2/1951 | Murphy ................. A61M 5/32 |
| | | | | 141/285 |
| 2,819,914 | A | | 1/1958 | Eitner |
| 3,367,366 | A | | 2/1968 | Oliveau |
| 3,692,029 | A | | 9/1972 | Adair |
| 3,750,667 | A | | 8/1973 | Pshenichny et al. |
| 3,777,771 | A | | 12/1973 | De Visscher |
| 3,848,645 | A | | 11/1974 | Franz |

(Continued)

FOREIGN PATENT DOCUMENTS

| CN | 101300039 A | 11/2008 |
| EP | 0174011 A2 | 3/1986 |

(Continued)

OTHER PUBLICATIONS

Supplementary European Search Report for Application No. 12774689. 9, dated Dec. 15, 2014, 6 pages.

(Continued)

*Primary Examiner* — Nicolas A Arnett

(74) *Attorney, Agent, or Firm* — McCarter & English, LLP

(57) ABSTRACT

A needle has a hollow shaft, a tip formed at one end of the shaft, one or more ports in fluid communication with the interior of the hollow shaft, and a closure. The closure and/or the shaft is movable between (i) a first position wherein the closure closes the port(s), and (ii) a second position opening the port(s).

48 Claims, 2 Drawing Sheets

(56) References Cited

U.S. PATENT DOCUMENTS

| | | | |
|---|---|---|---|
| 4,052,989 A * | 10/1977 | Kline | A61M 25/0606 |
| | | | 604/524 |
| 4,413,985 A | 11/1983 | Wellner et al. | |
| 4,421,146 A | 12/1983 | Bond et al. | |
| 4,610,469 A | 9/1986 | Wolff-Mooij | |
| 4,700,744 A | 10/1987 | Rutter et al. | |
| 4,752,292 A | 6/1988 | Lopez et al. | |
| 4,756,211 A | 7/1988 | Fellows | |
| 4,778,447 A | 10/1988 | Velde et al. | |
| 4,778,453 A | 10/1988 | Lopez | |
| 4,790,832 A | 12/1988 | Lopez | |
| 4,804,015 A | 2/1989 | Albinsson | |
| 4,816,024 A | 3/1989 | Sitar et al. | |
| 4,846,805 A | 7/1989 | Sitar | |
| 4,894,055 A | 1/1990 | Sudnak | |
| 4,917,149 A | 4/1990 | Grantham | |
| 4,931,048 A | 6/1990 | Lopez | |
| 4,938,390 A | 7/1990 | Markva | |
| 4,969,870 A | 11/1990 | Kramer et al. | |
| 5,012,845 A * | 5/1991 | Averette | G01N 35/1079 |
| | | | 141/130 |
| 5,049,136 A | 9/1991 | Johnson | |
| 5,104,382 A | 4/1992 | Brinkerhoff et al. | |
| 5,122,123 A | 6/1992 | Vaillancourt | |
| 5,176,643 A * | 1/1993 | Kramer | A61M 5/326 |
| | | | 604/272 |
| 5,199,947 A | 4/1993 | Lopez et al. | |
| 5,211,197 A | 5/1993 | Marrison et al. | |
| 5,261,891 A | 11/1993 | Brinkerhoff et al. | |
| 5,271,744 A | 12/1993 | Kramer et al. | |
| 5,279,583 A | 1/1994 | Shober, Jr. et al. | |
| 5,281,206 A | 1/1994 | Lopez | |
| 5,312,364 A | 5/1994 | Jacobs | |
| 5,344,414 A | 9/1994 | Lopez et al. | |
| 5,374,252 A * | 12/1994 | Banks | A61B 17/3496 |
| | | | 604/274 |
| 5,380,306 A | 1/1995 | Brinon | |
| 5,387,197 A | 2/1995 | Smith et al. | |
| 5,429,256 A | 7/1995 | Kestenbaum | |
| 5,451,210 A | 9/1995 | Kramer et al. | |
| 5,478,328 A | 12/1995 | Silverman et al. | |
| 5,482,083 A | 1/1996 | Jenski | |
| 5,492,147 A | 2/1996 | Challender et al. | |
| 5,520,666 A | 5/1996 | Choudhury et al. | |
| 5,531,692 A * | 7/1996 | Rogers | A61M 5/3287 |
| | | | 604/110 |
| 5,549,577 A | 8/1996 | Siegel et al. | |
| 5,575,804 A | 11/1996 | Yoon | |
| 5,584,848 A | 12/1996 | Yoon | |
| 5,607,439 A * | 3/1997 | Yoon | A61B 17/3417 |
| | | | 604/164.11 |
| 5,645,556 A | 7/1997 | Yoon | |
| 5,669,891 A | 9/1997 | Vaillancourt | |
| 5,685,852 A * | 11/1997 | Turkel | A61B 17/3401 |
| | | | 604/512 |
| 5,694,686 A | 12/1997 | Lopez | |
| 5,713,874 A | 2/1998 | Ferber | |
| 5,810,768 A | 9/1998 | Lopez | |
| 5,810,792 A | 9/1998 | Fangrow, Jr. et al. | |
| 6,032,691 A | 3/2000 | Powell et al. | |
| 6,041,805 A * | 3/2000 | Gydesen | F16L 37/35 |
| | | | 137/614.04 |
| 6,071,270 A * | 6/2000 | Fowles | A61J 1/2089 |
| | | | 137/614.04 |
| 6,079,444 A | 6/2000 | Harris et al. | |
| 6,113,068 A | 9/2000 | Ryan | |
| 6,113,583 A | 9/2000 | Fowles et al. | |
| 6,135,150 A | 10/2000 | Powell et al. | |
| 6,135,167 A * | 10/2000 | Kiholm | B67C 3/2637 |
| | | | 141/157 |
| 6,183,442 B1 | 2/2001 | Athanasiou et al. | |
| 6,245,048 B1 | 6/2001 | Fangrow, Jr. et al. | |
| 6,299,131 B1 | 10/2001 | Ryan | |
| 6,394,992 B1 | 5/2002 | Sjoholm | |
| 6,428,520 B1 | 8/2002 | Lopez et al. | |
| 6,478,775 B1 | 11/2002 | Galt et al. | |
| 6,497,686 B1 | 12/2002 | Adams et al. | |
| 6,554,146 B1 | 4/2003 | DeGroff et al. | |
| 6,599,273 B1 | 7/2003 | Lopez | |
| 6,604,561 B2 | 8/2003 | Py | |
| 6,685,674 B2 | 2/2004 | Douglas et al. | |
| 6,695,817 B1 | 2/2004 | Fangrow, Jr. | |
| 6,726,672 B1 | 4/2004 | Hanly et al. | |
| 6,742,556 B1 * | 6/2004 | Osuna | B67C 3/2637 |
| | | | 141/264 |
| 6,837,878 B2 | 1/2005 | Smutney et al. | |
| 6,866,158 B1 | 3/2005 | Sommer et al. | |
| 6,989,003 B2 | 1/2006 | Wing et al. | |
| 6,994,315 B2 | 2/2006 | Ryan et al. | |
| 7,032,631 B2 | 4/2006 | Py | |
| 7,077,176 B2 | 7/2006 | Py | |
| 7,099,731 B2 | 8/2006 | Lopez | |
| 7,100,646 B2 | 9/2006 | Py et al. | |
| 7,156,826 B2 | 1/2007 | Ishil et al. | |
| 7,174,914 B2 | 2/2007 | Ooishi et al. | |
| 7,309,326 B2 | 12/2007 | Fangrow, Jr. | |
| 7,354,427 B2 | 4/2008 | Fangrow | |
| 7,507,227 B2 | 3/2009 | Fangrow | |
| 7,510,547 B2 | 3/2009 | Fangrow | |
| 7,510,548 B2 | 3/2009 | Fangrow | |
| 7,513,895 B2 | 4/2009 | Fangrow | |
| 7,534,239 B1 | 5/2009 | Schneider et al. | |
| 7,547,300 B2 | 6/2009 | Fangrow | |
| 7,568,509 B2 | 8/2009 | Py | |
| 7,569,043 B2 | 8/2009 | Fangrow | |
| 7,645,271 B2 | 1/2010 | Fangrow | |
| 7,648,491 B2 | 1/2010 | Rogers | |
| 7,654,995 B2 | 2/2010 | Warren et al. | |
| 7,658,733 B2 | 2/2010 | Fangrow | |
| 7,670,322 B2 | 3/2010 | Fangrow, Jr. | |
| 7,722,576 B2 | 5/2010 | Lopez | |
| 7,758,566 B2 | 7/2010 | Simpson et al. | |
| 7,803,139 B2 | 9/2010 | Fangrow, Jr. | |
| 7,824,393 B2 | 11/2010 | Fangrow | |
| 7,883,499 B2 * | 2/2011 | Fangrow | A61J 1/1406 |
| | | | 604/407 |
| 7,892,216 B2 | 2/2011 | Fangrow, Jr. | |
| 7,931,615 B2 | 4/2011 | Fangrow, Jr. | |
| 8,105,314 B2 | 1/2012 | Fangrow, Jr. | |
| 8,196,606 B2 | 6/2012 | Kitagawa | |
| 8,246,578 B2 | 8/2012 | Matsumoto | |
| 8,348,881 B2 | 1/2013 | Aubert et al. | |
| 8,409,164 B2 | 4/2013 | Fangrow | |
| 8,454,579 B2 | 6/2013 | Fangrow, Jr. | |
| 8,522,832 B2 | 9/2013 | Lopez et al. | |
| 8,535,279 B2 | 9/2013 | Schweikert et al. | |
| 8,552,832 B2 | 10/2013 | Kohanek | |
| 8,647,310 B2 | 2/2014 | Fangrow, Jr. et al. | |
| 8,696,625 B2 | 4/2014 | Carrel et al. | |
| 8,758,306 B2 | 6/2014 | Lopez et al. | |
| 8,759,306 B2 | 6/2014 | Kaletta | |
| 8,808,200 B2 | 8/2014 | Miller et al. | |
| 8,956,330 B2 | 2/2015 | Fangrow, Jr. | |
| 10,017,286 B2 * | 7/2018 | Py | B65B 3/003 |
| 10,850,882 B2 * | 12/2020 | Py | B65B 39/004 |
| 2002/0032433 A1 | 3/2002 | Lopez | |
| 2002/0120212 A1 | 8/2002 | Ritchart et al. | |
| 2002/0131902 A1 | 9/2002 | Levy | |
| 2002/0188260 A1 | 12/2002 | Gollobin | |
| 2002/0189712 A1 | 12/2002 | Safabash | |
| 2003/0032940 A1 | 2/2003 | Doyle | |
| 2003/0070726 A1 | 4/2003 | Andreasson et al. | |
| 2003/0106610 A1 | 6/2003 | Roos et al. | |
| 2003/0216667 A1 | 11/2003 | Viola | |
| 2004/0124389 A1 | 7/2004 | Phillips | |
| 2004/0222224 A1 * | 11/2004 | Plester | B67C 7/008 |
| | | | 220/203.18 |
| 2004/0256026 A1 | 12/2004 | Py | |
| 2006/0142735 A1 | 6/2006 | Whitley | |
| 2006/0178646 A1 | 8/2006 | Harris et al. | |
| 2006/0287639 A1 * | 12/2006 | Sharp | A61J 1/2096 |
| | | | 604/415 |
| 2007/0106225 A1 | 5/2007 | Millerd | |

(56) References Cited

U.S. PATENT DOCUMENTS

| | | |
|---|---|---|
| 2007/0225635 A1 | 9/2007 | Lynn |
| 2008/0103487 A1 | 5/2008 | Miyasaka |
| 2008/0197626 A1 | 8/2008 | Coambs et al. |
| 2009/0082725 A1 | 3/2009 | Witowski |
| 2009/0091129 A1 | 4/2009 | Moriiki et al. |
| 2009/0243281 A1 | 10/2009 | Seifert et al. |
| 2009/0292274 A1 | 11/2009 | Guala |
| 2010/0021230 A1 | 1/2010 | Olivier |
| 2010/0108681 A1* | 5/2010 | Jepson ............... A61M 39/1011 220/278 |
| 2010/0121305 A1 | 5/2010 | Rogers |
| 2010/0140290 A1 | 6/2010 | Py |
| 2011/0060312 A1 | 3/2011 | Scheurer |
| 2011/0106046 A1 | 5/2011 | Hiranuma et al. |
| 2011/0186764 A1 | 8/2011 | Takami |
| 2011/0240158 A1 | 10/2011 | Py |
| 2012/0042971 A1 | 2/2012 | Py |
| 2012/0118416 A1 | 5/2012 | Johnson |
| 2012/0220978 A1 | 8/2012 | Lev et al. |
| 2012/0261027 A1* | 10/2012 | Py ........................ B65B 39/004 141/2 |
| 2013/0046246 A1 | 2/2013 | Cross et al. |
| 2013/0333796 A1* | 12/2013 | Py ........................ A61J 1/1425 141/1 |
| 2014/0311617 A1* | 10/2014 | Py ........................ A61J 1/1425 141/89 |

FOREIGN PATENT DOCUMENTS

| | | |
|---|---|---|
| RU | 2178741 C2 | 1/2002 |
| WO | 1993/11828 A1 | 6/1993 |
| WO | 1995/05863 A1 | 3/1995 |
| WO | 2009/035383 A1 | 3/2009 |
| WO | 2011/146012 A1 | 11/2011 |

OTHER PUBLICATIONS

International Search Report and Written Opinion for Application No. PCT/US2012/034127, dated Aug. 23, 2012, 8 pages.

* cited by examiner

NEEDLE WITH CLOSURE AND METHOD

CROSS-REFERENCE TO RELATED APPLICATIONS

This patent application is a continuation of U.S. patent application Ser. No. 13/450,306, filed Apr. 18, 2012, claiming benefit under 35 U.S.C. § 119(e) to U.S. Provisional Patent Application Ser. No. 61/476,523, entitled "Filling Needle and Method," filed Apr. 18, 2011, which are hereby expressly incorporated by reference in its entirety as part of the present disclosure.

FIELD OF THE INVENTION

The present invention relates to needles, and more particularly, relates to filling needles and methods of filling with needles.

BACKGROUND INFORMATION

A typical prior art filling needle includes a hollow stainless steel shaft, a non-coring, conically-pointed tip fixedly secured to the distal end of the shaft, and diametrically opposed fluid ports proximal to the tip and in fluid communication between the interior of the shaft and the ambient atmosphere. One drawback encountered with prior art filling needles is that the interior of the needle, and any fluid contained therein, is exposed to the ambient atmosphere through the open fluid ports. Even though the needle ports or eyes are very small, the incidence of contamination in aseptic filling is such that there still can be a need to control the environment in prior art filling machines in order to protect the filling needles, and particularly the end opening(s) of the filling needles, regardless of type. If the ambient atmosphere is contaminated, the open ports can allow the interior of the needle and any fluid passing therethrough to become contaminated. On the other hand, if the needle is used to dispense a contaminated fluid, or a fluid that might be harmful if it is exposed to or comes into contact with a person, the open ports can allow such fluid to contaminate its ambient atmosphere or potentially harm a person that contacts the needle or is in the vicinity thereof. In prior art filling machines, including the needle filling and laser resealing machines described in the present inventor's U.S. Pat. No. 6,604,561, the regulatory agencies require control of the needle environment in order to protect against any exposure of the product itself to the environment and the resulting contamination of the product that might occur. Accordingly, the surfaces that may come into contact with the product, including the surfaces of the stopper and vial, are protected from the environment until the closed vial is pierced by the sterile needle. But, if for whatever reason, the latter were to be contaminated, a risk of contaminating the product inside the vial would exist.

It is an object of the present invention to overcome one or more of the above-described drawbacks and/or disadvantages of the prior art, including to reduce the risk of contamination and/or to reduce the controls over, or the need to control a filling needle environment.

SUMMARY OF THE INVENTION

In accordance with a first aspect, a needle comprises a hollow shaft; a tip formed at one end of the shaft; a port in fluid communication with the interior of the hollow shaft; and a closure. The closure and/or the shaft is movable between (i) a first position wherein the closure closes the port, and (ii) a second position opening the port. To prevent contamination of the needle from external sources, the closure may be configured to provide a substantially fluid-tight and/or airtight or hermetic seal between the port and ambient atmosphere in the closed position.

In some embodiments, the closure is biased in the direction from the second position to the first position to normally close the port. In some such embodiments, the needle includes a biasing member, e.g., a spring, biasing the closure in the direction from the second position to the first position.

In some embodiments, the closure is engageable with a penetrable septum to move the closure and/or the shaft from the first position wherein the closure closes the port, to the second position opening the port, upon penetrating the septum with the needle. In some such embodiments, at least one of the closure and the shaft is movable from the second position wherein the port is opened, to the first position wherein the port is closed, during or upon withdrawing the needle from the septum.

In some embodiments, the closure extends annularly about the shaft. In some embodiments, the closure includes a flange on one end thereof engageable with a biasing member or spring for biasing the closure in the direction from the second position to the first position. An opposite end of the closure is engageable with a stop surface of the needle to stop the closure in the first position. In some embodiments, a distal end of the closure is substantially flush with an adjacent portion of the needle tip. In some embodiments, the tip is defined by a non-coring, conically-pointed tip.

In accordance with another aspect, a needle comprises first means for providing a conduit for the passage of fluid therethrough; second means formed at one end of the first means for penetrating a septum; third means in fluid communication with the conduit for passage of fluid from the conduit therethrough; and fourth means for closing the third means. The fourth means and/or the first means is movable between (i) a first position wherein the fourth means closes the third means, and (ii) a second position opening the third means. In some embodiments, the first means is a needle shaft, the second means is a needle tip, the third means is a port, and the fourth means is a closure.

In accordance with another aspect, a method comprising the following steps:
(i) piercing a septum with a needle and placing the needle in fluid communication with a chamber;
(ii) during or after the piercing step, moving a closure and/or a filling port of the needle from a closed position closing the filling port to an open position opening the filling port; and
(iii) introducing fluid from the needle into the chamber after full perforation of the septum and/or after the needle port(s) or eye(s) have passed through the interior surface of the septum and are located within the chamber.

In accordance with another aspect, the method further comprises the following steps:
(iv) withdrawing the needle from the septum; and
(v) before and/or during the withdrawing step, moving the closure and/or the filling port of the needle from the open position to the closed position.

Some embodiments further comprise substantially sealing the filling port from ambient atmosphere in the closed position. Some embodiments further comprise substantially preventing any contact between the filling port and the septum during the penetrating and withdrawing steps. Some such embodiments further comprise interposing the closure between the filling port and septum to substantially prevent any contact between the filling port and septum.

Some embodiments further comprise the step of sealing the resulting penetration aperture in the septum. In these embodiments the self-closing properties of the septum material are engineered in a manner known to those of ordinary skill in the pertinent art based on the teachings herein to prevent any opening or passage between the needle and the pierced septum material, or any passage between the interior of the filling machine and the sterile chamber of the container or device to be filled after the septum is pierced. One objective and/or advantage of such embodiments is to demonstrate that the sterile container is always closed from its ambient environment even when mechanically opened by the filling needle so that after piercing and withdrawal of the needle, the visco-elastic or self-closing properties of the septum are such that any opening in the residual penetration aperture would be less than or equal to about 0.05 micrometer, such as less than or equal to about 0.02 micrometer, or even less than or equal to about 0.01 micrometer, or otherwise at a size that prevents fluid, including air, from penetrating through the resulting penetration aperture, prior to resealing thereof. In some such embodiments, the sealing step includes applying radiation or energy to the septum. In some embodiments, the sealing step includes at least one of thermal sealing, laser sealing and liquid sealant sealing. An exemplary liquid sealant is silicone. In some such embodiments, the liquid silicone is over-molded onto a compatible septum and/or cap material to ensure seal integrity and durability and enhance safety standards.

Some embodiments further comprise performing the penetrating, filling and withdrawing steps in a non-sterile or relatively low sterility assurance level ("SAL") environment, such as about log 3 or lower, including about log 2 or about log 1; filling a sterile fluid through the needle and into the chamber; and maintaining the sterility of the filled fluid throughout the penetrating, filling and withdrawing steps. Some embodiments further comprise sealing a resulting penetration aperture in the septum and maintaining the sterility of the filled fluid during the sealing step.

One advantage of the present invention is that the closure closes the needle port(s) with respect to ambient atmosphere thereby preventing contamination of the needle port and interior of the needle and, in turn, preventing contamination of fluid flowing therethrough. Another advantage of certain embodiments is that they allow sterile filling within a non-aseptic, non-sterile or relatively low SAL environment (e.g., about log 3 or lower) while nevertheless sterile filling fluids into containers or devices and hermetically resealing them. Accordingly, the filling of a non-preserved or preservative-free formulation with a self-closing filling needle of the present invention without control of the filling needle environment, or with reduced needle environment controls, can be safer than filling a preserved formulation in an aseptically-controlled environment with prior art filling apparatus and methods. Yet another advantage of some embodiments is that the closure is interposed between the needle port and a septum to prevent contact between the needle port and septum, and thereby further prevent any contamination of the needle port and interior of the needle and of any fluid flowing therethrough. In some embodiments, the combination of the self-closing needle, such as the needle with "sliding shutter" closure, and a liquid silicone drop ("LSD") or other resealable septum, creates a unique system and method allowing for the reduction or elimination of environmental controls required by prior art sterile filling systems and methods, thereby allowing for a simplification in equipment, a reduction in the time associated with setup and operation of the equipment, and/or a reduction in the cost of equipment and/or aseptic filling and processing. As a consequence, devices and methods of the invention facilitate the ability of manufacturers of any size, including small entity manufacturers, to safely fill preserved or preservative-free formulations into aseptic environments, and to do so at a lower cost, with improved efficiency and/or in less time, than required by prior art aseptic filling devices and methods.

Other objects and advantages of the present invention, and/or of the currently preferred embodiments thereof, will become more readily apparent in view of the following detailed description and the accompanying drawings.

DETAILED DESCRIPTION OF EMBODIMENTS OF THE INVENTION

Figure 1:
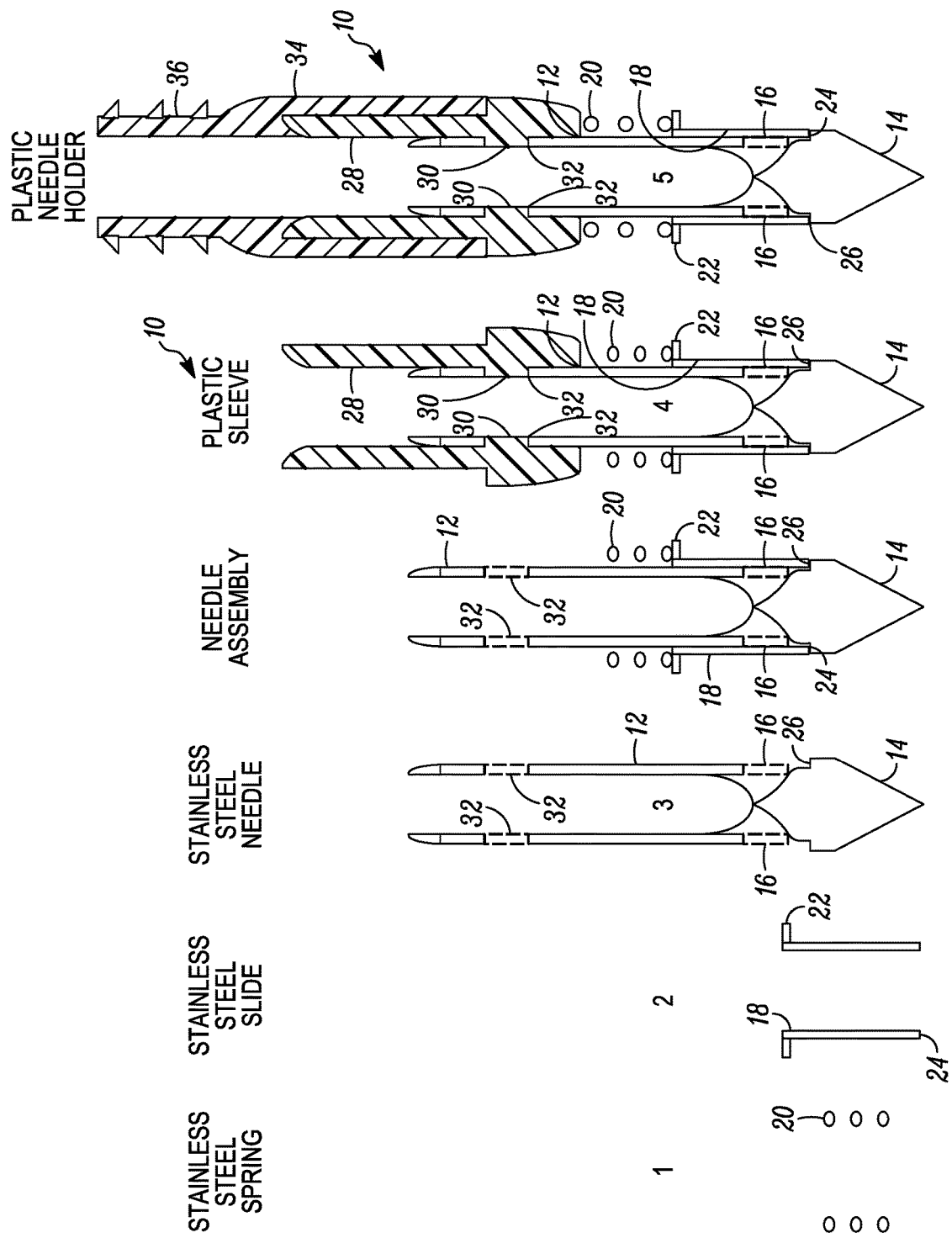
FIG. 1 is a sequential, cross-sectional view of a needle showing the separate components of the needle, and the assembly thereof.
Figure 2:
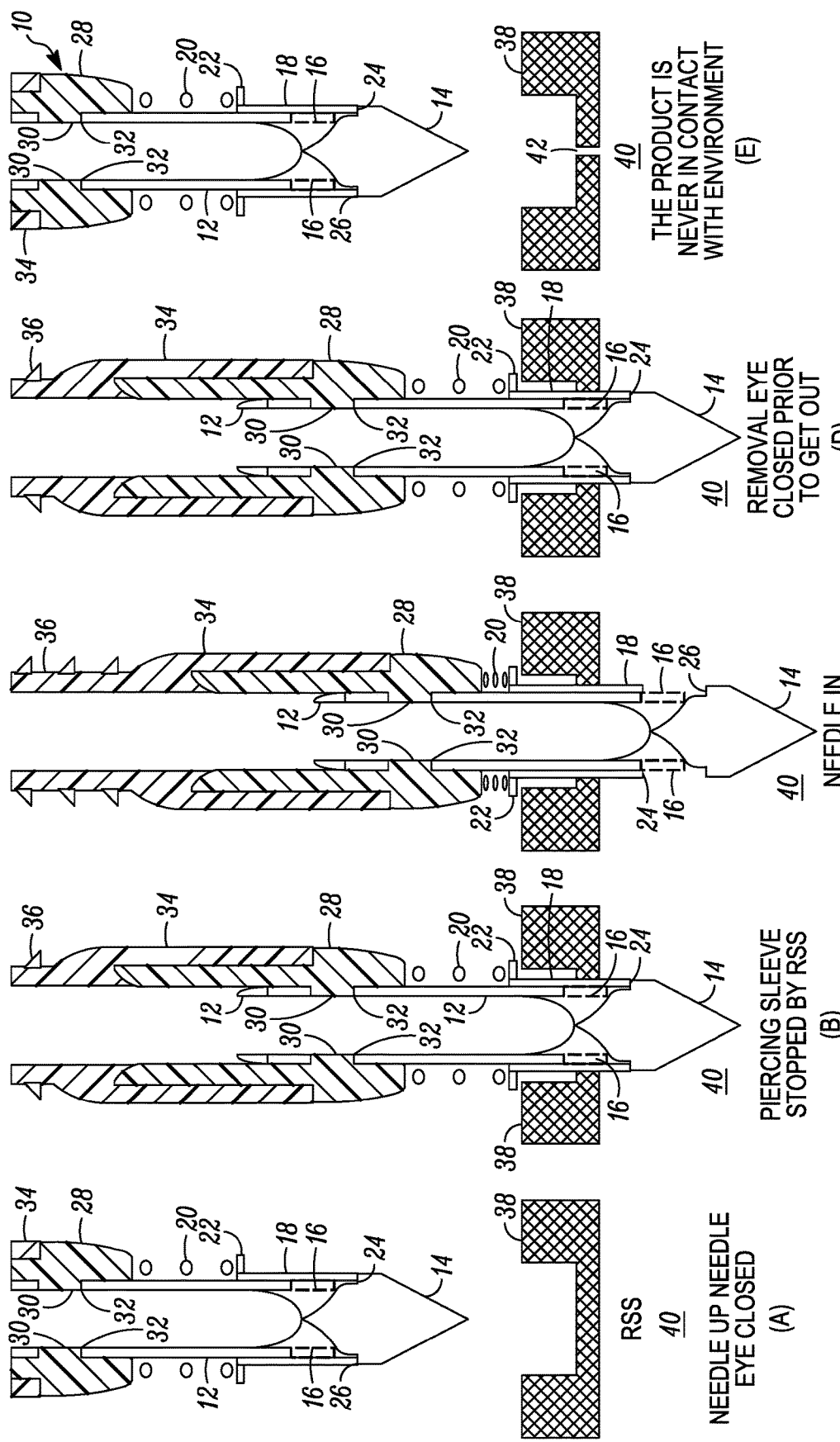
FIGS. 2A through 2E are sequential cross-sectional views of the needle of FIG. 1 showing the needle during penetration of and withdrawal from a resealable septum for filling a device or chamber of a device through such resealable septum.

In FIGS. 1 and 2, a needle is indicated generally by the reference numeral 10. The needle 10 comprises a hollow shaft 12, a tip 14 formed at one end of the shaft; two ports 16, 16 in fluid communication with the interior of the hollow shaft 12, and a closure 18. In the illustrated embodiments, the two ports 16 are diametrically opposed relative to each other; however, as may be recognized by those of ordinary skill in the pertinent art based on the teachings herein, the needle may define any number of ports that may define any of numerous different configurations and locations. The closure 18 and/or the shaft 12 is movable between (i) a first position wherein the closure closes the ports 16, as shown typically in FIG. 1, and (ii) a second position opening the ports 16, as shown typically in FIG. 2C. In the illustrated embodiment, when in the closed position, the closure 18 forms a substantially fluid-tight seal between the ports 16 and ambient atmosphere. The closure 18 is biased in the direction from the second or open position to the first or closed position to normally close the ports 16. In the illustrated embodiment, the needle 10 includes a coil spring 20 that biases the closure in the direction from the second or open position to the first or closed position. As may be recognized by those of ordinary skill in the pertinent art based on the teachings herein, the closure may be biased in any of numerous different ways that are currently known or that later become known, using biasing members other than springs, and if a spring is used, any of numerous different springs or combinations of springs may be used. In the illustrated embodiment, the closure 18 is an axially or vertically sliding "shutter" closure that slides axially over the needle shaft 12 between the normally closed and open positions. However, as may be recognized by those of ordinary skill in the pertinent art based on the teachings herein, the closure may take any of numerous different configurations that are currently known, or that later become known, for performing the function of the closure as described herein.

The closure 18 extends both annularly and axially about the shaft 12 and is slidably mounted on the shaft. The closure 18 includes an annular flange 22 on one end thereof that is engageable with the spring 20 for biasing the closure in the direction from the second or open position to the first or closed position. An opposite end 24 of the closure 18 is engageable with an annular stop surface 26 of the needle tip to stop the closure in the first or closed position. The distal end 24 and substantially cylindrical body of the closure 18 are substantially flush with the perimeter of the stop surface 26 and adjacent portion of the needle tip 14. The annular flange 22, on the other hand, projects radially outwardly to provide a surface for seating and engaging the distal end of the spring 20. In the illustrated embodiment, the needle tip 14 is defined by a non-coring, conically-pointed tip; however, as may be recognized by those of ordinary skill in the pertinent art based on the teachings herein, the needle tip may define any of numerous other needle tip configurations that are currently known, or that later become known, such as a trocar tip. In one configuration, the spring force of the spring 20 is sufficient to allow the needle to penetrate the septum while maintaining the closure 18 in the closed position during penetration of the closure through the septum and until the annular flange 22 of the closure engages an exterior surface of the septum (or other exterior or stop surface of the device) to cause relative movement of the closure and shaft against the bias of the spring from the normally closed position to the open position and, in turn, expose the sterile needle ports to the sterile device chamber.

An axially-elongated flange 28 includes bosses 30 that are received within corresponding apertures 32 formed in the needle shaft 12 to fixedly secure the flange to the shaft. A needle holder 34 is secured to the flange 28 and includes a barbed fitting 36 for attachment to a filling line (not shown). In the illustrated embodiment, the flange 28 is over-molded to the end of the shaft 12, and the needle holder 34 is over-molded to the flange 28. The coil spring 20 is mounted between the distal end of the axially-elongated flange 28 and the closure annular flange 22. As may be recognized by those of ordinary skill in the pertinent art based on the teachings herein, any of numerous different types of fittings or connections that are currently known, or that later become known, equally may be employed for connecting the needle to a filling or other type of line or conduit.

As shown typically in FIG. 2, the needle 10 may be used to aseptically or sterile fill fluids through a penetrable septum 38 into a chamber 40 of a container or other device (not shown). As shown in FIG. 2A, prior to penetrating the septum 38, and when the needle tip 14 is exposed to the ambient atmosphere, the closure 18 is in the closed position sealing the ports 16 with respect to ambient atmosphere to thereby maintain the sterility of the ports and of the interior of the needle. As shown in FIG. 2B, upon penetrating the septum 38, the closure 18 is interposed between the ports 16 and the septum 38 to substantially prevent contact between the ports and the septum. Then, as shown in FIG. 2C, when the ports 16 are located within the chamber 40, the annular flange 22 of the closure engages the septum, and/or the frictional engagement between the cylindrical body of the closure 18 and the septum 38, prevents further movement of the closure relative to the septum. Further penetration of the needle 10 into the septum 38 causes the shaft 12 and needle tip 14 to move relative to the closure 18 against the bias of the spring 20 to, in turn, move the ports 16 to the open position. In the open position of FIG. 2C, the fluid within the needle is permitted to flow through the open ports 16 and into the chamber 40. Since the sterile ports 16 are not exposed to the ambient atmosphere, the ports, interior of the needle, and fluid flowing therethrough, are not contaminated and/or are maintained sterile as the fluid is injected or otherwise dispensed into the chamber 40. After the chamber 40 is filled as desired, and as shown typically in FIG. 2D, the needle 10 is withdrawn from the septum 38. As the needle is withdrawn, the spring 20 biases the closure 18 downwardly or in the direction of the septum 38. Therefore, as the needle shaft 12 is withdrawn, it is moved axially relative to the closure 18 to, in turn, move the ports 16 into the closed position behind the closure. The sliding shutter or closure 18 may be configured to substantially prevent contact between the needle eyes or ports 16, and the sliding shutter or closure is closed over the needle eyes or ports prior to their passage through the septum and/or withdrawal therefrom. When the end 24 of the closure 18 engages the stop surface 26 of the needle tip, the closure is fixed in the closed position, and is maintained in the closed position by the downward force or bias of the spring 20. Thus, during and upon, and/or before, withdrawal of the needle 10 from the septum 38, the closure 18 closes the ports 16 and prevents any contamination of the ports or interior of the needle. In some embodiments, the septum 38 is engineered to self-close and thereby ensure that the head loss left by the residual needle aperture 42 after the tip of the needle is withdrawn prevents any fluid ingress therethrough.

As shown typically in FIG. 2E, although the septum may be self-closing as described above, the resulting needle or penetration aperture 42 in the septum may be resealed by a further process. Such processes include mechanically (such as by an overlying cover (not shown)), by applying radiation or energy to the septum, e.g., thermal resealing, by laser resealing, or by applying a liquid sealant thereto, which may be cured at room temperature or by applying radiation or energy to the sealant, such as a silicone or silicon-based sealant, e.g., UV (ultraviolet) or visible light curable composition, to form a fluid tight or hermetic seal and thereby maintain the sterility of the filled fluid in the chamber. Examples of resealable septums and processes for resealing them are described, for example, in the following patents and applications that are incorporated by reference in their entirety herein: U.S. patent application Ser. No. 08/424,932, filed Apr. 19, 1995, entitled "Process for Filling a Sealed Receptacle under Aseptic Conditions," issued as U.S. Pat. No. 5,641,004; U.S. patent application Ser. No. 09/781,846, filed Feb. 12, 2001, entitled "Medicament Vial Having a Heat-Sealable Cap, and Apparatus and Method for Filling Vial," issued as U.S. Pat. No. 6,604,561, which, in turn, claims priority from U.S. Provisional Patent Application Ser. No. 60/182,139, filed Feb. 11, 2000, entitled "Heat-Sealable Cap for Medicament Vial;" U.S. patent application Ser. No. 10/655,455, filed Sep. 3, 2003, entitled "Sealed Containers and Methods of Making and Filling Same," issued as U.S. Pat. No. 7,100,646, which, in turn, claims priority from similarly titled U.S. Provisional Patent Application Ser. No. 60/408,068, filed Sep. 3, 2002; U.S. patent application Ser. No. 10/766,172, filed Jan. 28, 2004, entitled "Medicament Vial Having a Heat-Sealable Cap, and Apparatus and Method for Filling the Vial," issued as U.S. Pat. No. 7,032,631, which, in turn claims priority from similarly titled U.S. Provisional Patent Application Ser. No. 60/443,526, filed Jan. 28, 2003 and similarly titled U.S. Provisional Patent Application Ser. No. 60/484,204, filed Jun. 30, 2003; U.S. Provisional Patent Application entitled "Modular Filling Apparatus and Method," filed Apr. 13, 2012; U.S. patent application Ser. No. 12/901,420, entitled "Device with Co-Molded Closure, One-Way Valve and Variable Volume Storage Chamber and Related Method," filed Oct. 8, 2010, which, in turn, claims priority to similarly titled U.S. Provisional Patent Application Ser. No. 61/250,363, filed Oct. 9, 2009. The process then may be repeated whereby the same needle 10 may be used to aseptically or sterile fill plural or numerous chambers of devices.

When filling a sterile product, the self-closing septum 38 prevents the filled product from being contaminated by the device environment. In other applications, the self-closing septum prevents the product itself from contaminating its environment. For example, some products, such as cytotoxic products for treating cancer, or radioactive products, are hazardous and/or can be dangerous to operators, treatment professionals or other persons that might need to handle the filling machine or filled devices. Prior art equipment for handling such dangerous substances can be complex and costly. One advantage of the self-closing needle technology of the present invention is that it allows such dangerous or hazardous products to be filled and handled in a relatively safe and less costly manner than encountered in the prior art.

In another embodiment, the filling machine includes a first needle for piercing the septum (not shown), and a second self-closing needle for piercing the septum through the resulting penetration aperture formed by the first needle. In this embodiment, the first needle may be a solid needle without any lumen or closure, and may define a different diameter than the second needle, such as a smaller diameter. The first needle may be located in a first station and the second needle may be located in a second station, wherein the devices with septums are transported from the first station to the second station on a motorized conveyor. Each station may include an over pressure of sterile air or other gas. Alternatively, the first and second needles may be located in the same station on a common manifold or fixture to reduce the system footprint and/or to facilitate alignment of the second needle with the penetration aperture of the first needle. As described above, the septum is formed of a visco-elastic material that self-closes after withdrawal of each needle therefrom, and therefore prevents any contamination of the interior of the device between the first and second needle penetrations, and between the second needle penetration and resealing of the resulting penetration aperture. One advantage of this embodiment is that the penetration aperture formed by the first needle reduces that frictional force encountered by the second needle and closure during passage through the septum, and therefore reduces the spring force required to maintain the closure in the normally closed position during septum penetration.

As may be recognized by those of ordinary skill in the pertinent art based on the teachings herein, numerous changes and modifications may be made to the above-described and other embodiments of the present invention without departing from its scope as defined in the appended claims. For example, the needle, closure, spring of biasing member and holder may be made of any of numerous different metals or plastics that are currently known or that later become known. The term "needle" is used herein to mean any of numerous different types of devices that are used to penetrate and introduce matter into, or withdraw matter from, an object, such as a chamber or device, that are currently known, or that later become known. The term "septum" is used herein to mean any of numerous different types of needle penetrable septums, stoppers or other devices that are penetrable by a needle for filling a chamber therethrough. The needles may be used in sterile or non-sterile environments, to needle fill with or in accordance with any of numerous different filling devices or methods that are currently known, or that later become known. Accordingly, this detailed description of embodiments is to be taken in an illustrative, as opposed to a limiting sense.

What is claimed is:

1. A method comprising the following steps:
   transferring fluid between a device and a needle of a transfer system, wherein the device defines a chamber therein adapted to receive fluid therein and having an opening, and a pierceable septum in fluid communication with the chamber and sealing said opening, the transferring step including:
   piercing the septum with a needle adapted to pierce the septum and placing the needle in fluid communication with the chamber, the needle comprising a hollow shaft; a septum-piercing tip formed at a distal end of the shaft; at least one port in fluid communication with the interior of the hollow shaft; and a closure; wherein one or more of the closure or the shaft is movable between (i) a first position wherein the closure closes the at least one port to prevent passage of fluid through the at least one port and hermetically seal the at least one port with respect to ambient atmosphere, and (ii) a second position opening the at least one port to permit passage of fluid through the at least one port; and wherein a portion of the closure radially adjacent to the port is adapted to at least partially penetrate into or through the septum in the first position;
   after or during the piercing step, moving one or more of the closure or the shaft of the needle from the first position to the second position; and
   flowing fluid between the needle and the chamber.

2. A method as defined in claim 1, further comprising the following steps:
   withdrawing the needle from the septum; and
   before or during the withdrawing step, moving one or more of the closure or the shaft of the needle from the second position to the first position.

3. A method as defined in claim 2, wherein the fluid is flowed between the needle and the chamber after full perforation of the septum or after part of the at least one port has passed through an interior surface of the septum and is located in fluid communication with the chamber.

4. A method as defined in claim 3, wherein the fluid is flowed between the needle and the chamber after the at least one port is substantially completely located within the chamber.

5. A method as defined in claim 2, wherein the step of moving one or more of the closure or the shaft of the needle from the second position to the first position motion includes moving one or more of the closure or the shaft of the needle with a biasing member.

6. A method as defined in claim 2, wherein during the piercing and withdrawing steps, substantially preventing any contact between the at least one port and the septum.

7. A method as defined in claim 6, further comprising interposing the closure between the at least one port and septum to substantially prevent any contact between the at least one port and septum.

8. A method as defined in claim 2, further comprising the step of sealing a resulting penetration aperture in the septum.

9. A method as defined in claim 8, wherein the sealing step includes applying radiation or energy to the septum, thereby sealing the penetration aperture.

10. A method as defined in claim 8, wherein the sealing step includes one or more of thermal sealing, laser sealing or liquid sealant sealing.

11. A method as defined in claim 10, wherein the liquid sealant is silicone.

12. A method as defined in claim 2, wherein the fluid is sterile, the piercing, flowing and withdrawing steps are performed in a non-sterile environment or an environment defining a SAL of about log 3 or less and further comprising maintaining the sterility of the fluid throughout the piercing, flowing and withdrawing steps.

13. A method as defined in claim 12, further comprising sealing a resulting penetration aperture in the septum and maintaining the sterility of the fluid during the sealing step.

14. A method as defined in claim 2, further comprising piercing the septum with a first needle and withdrawing the first needle to create a resulting penetration aperture within the septum, and then performing said piercing step with said needle including the closure through the penetration aperture formed by the first needle.

15. A method as defined in claim 14, wherein the septum is self closing and substantially prevents the ingress of fluid through the resulting penetration aperture.

16. A method as defined in claim 1, further comprising, while the closure is in the first position, penetrating a portion of the closure extending along the at least one port in the first position entirely through the septum.

17. A method as defined in claim 1, further comprising penetrating entirely through the septum with the portion of the closure radially adjacent to the port in the first position.

18. A method as defined in claim 1, wherein the shaft defines a proximal end and a distal end, and the closure defines a surface located, in the first position, closer to the proximal end of the shaft than the portion of the port closest to the distal end of the shaft and adapted to engage the septum and thereby one or more of (a) cause relative movement of the closure and the shaft, or (b) prevent further movement of the closure relative to the septum, and the method further includes engaging the septum with the surface and subsequently performing the moving step.

19. A method as defined in claim 18, including performing the engaging step after at least a portion of the at least one port has entered the chamber.

20. A method as defined in claim 1, wherein (a) the closure is biased in a direction from the second position toward the first position to normally close the at least one port, and (b) when the closure is located in its most distal position relative to the shaft, one or more of (i) at least a portion of the tip is exposed to ambient atmosphere or (ii) the closure does not enclose at least a portion of the tip.

21. A transfer system comprising:
   a device defining a chamber therein adapted to receive fluid therein and having an opening, and a pierceable septum in fluid communication with the chamber and sealing said opening; and
   a needle comprising
      a hollow shaft;
      a septum-piercing tip formed at one end of the shaft;
      at least one port in fluid communication with the interior of the hollow shaft; and
      a closure;
   wherein the needle is adapted to pierce the septum;
   wherein one or more of the closure or the shaft is movable between (i) a first position wherein the closure closes the at least one port to prevent passage of fluid through the at least one port and hermetically seal the at least one port with respect to ambient atmosphere, and (ii) a second position opening the at least one port to permit passage of fluid through the at least one port; and
   wherein a portion of the closure radially adjacent to the port is adapted to at least partially penetrate into or through the septum in the first position.

22. A system as defined in claim 21, wherein, when the closure is located in its most distal position relative to the shaft, one or more of (i) at least a portion of the tip is exposed to ambient atmosphere or (ii) the closure does not enclose at least a portion of the tip.

23. A system as defined in claim 21, wherein a diameter of the closure at a distal end thereof is no greater than a maximum diameter of the tip.

24. A system as defined in claim 21, further comprising a biasing member adapted to bias the closure in a direction from the second position toward the first position during penetration of the closure into or through the septum.

25. A system as defined in claim 21 adapted so that a portion of the closure extending along the at least one port in the first position is adapted to at least partially penetrate into or through the septum in the first position.

26. A system as defined in claim 21, wherein along an entire length of the at least one port and in the first position, the needle defines a straight outermost surface thereof.

27. A system as defined in claim 21, wherein the closure is biased in a direction from the second position toward the first position to normally close the at least one port.

28. A system as defined in claim 21, wherein the closure is engageable with the septum to move one or more of the closure or the shaft from the first position wherein the closure closes the at least one port to prevent passage of fluid through the at least one port, to the second position opening the at least one port to permit passage of fluid through the at least one port, upon piercing the septum with the needle.

29. A system as defined in claim 28, wherein one or more of the closure or the shaft is movable from the second position wherein the at least one port is opened to permit passage of fluid through the at least one port, to the first position wherein the at least one port is closed to prevent passage of fluid through the at least one port, during or upon withdrawing the needle from the septum.

30. A system as defined in claim 21, wherein the closure extends annularly about the shaft.

31. A system as defined in claim 21, wherein the closure includes a flange or projection engageable with a biasing member for biasing the closure in a direction from the second position toward the first position.

32. A system as defined in claim 31, wherein an end of the closure is engageable with a stop surface of the needle to stop the closure in the first position.

33. A system as defined in claim 32, wherein an exposed outer surface of the closure extends from the stop surface to the flange or projection.

34. A system as defined in claim 21, wherein a distal end of the closure is flush with an adjacent portion of the needle tip.

35. A system as defined in claim 21, wherein the tip is defined by a non-coring, conically-pointed tip.

36. A system as defined in claim 21, further comprising a holder connected to an end of the shaft opposite the tip and engageable in fluid communication with a filling line for introducing fluid from the filling line through the needle.

37. A system as defined in claim 36, wherein the holder is over-molded to the shaft.

38. A system as defined in claim 21, wherein a diameter of the closure at a distal end thereof is no greater than a maximum diameter of the tip.

39. A system as defined in claim 21, wherein the shaft defines a proximal end and a distal end, and the closure defines a surface located, in the first position, closer to the proximal end of the shaft than the portion of the port closest to the distal end of the shaft and adapted to engage the septum and thereby one or more of (a) cause relative movement of the closure and the shaft, or (b) prevent further movement of the closure relative to the septum.

40. A system as defined claim 39, wherein the surface is defined by a projection or flange of the closure.

41. A system as defined in claim 39, wherein the surface is axially spaced from a distal end of the at least one port a distance at least equal to a thickness of the septum to be pierced by the needle.

42. A system as defined in claim 21, wherein the septum defines an aperture therethrough configured to receive at least a portion of the shaft and the closure during engagement of the first device and the second device, and the closure is adapted to at least partially penetrate into or through the aperture in the first position.

43. An apparatus as defined in claim 42, wherein the septum is self-closing and defines a closed position substantially preventing one or more of fluid or contamination from passing or penetrating through the aperture.

44. An apparatus as defined in claim 42 adapted so that one or more of (i) a portion of the closure extending along the at least one port in the first position is adapted to at least partially penetrate into or through the aperture in the first position; (ii) during at least a portion of said at least partial penetration of the closure into or through the aperture, the at least one port is prevented from contacting the septum; or (iii) during at least a portion of said at least partial penetration of the closure into or through the aperture, the closure is interposed between the at least one port and the septum.

45. A method comprising:
    engaging a first device and a second device,
        the first device defining a chamber therein adapted to receive fluid therein and having an opening, and comprising a pierceable septum in fluid communication with the chamber and sealing said opening;
        the second device comprising
            a needle comprising
                a hollow shaft;
                a septum-piercing tip formed at one end of the shaft;
                at least one port in fluid communication with an interior of the hollow shaft; and
            a closure;
            wherein the needle is adapted to pierce the septum;
            wherein one or more of the closure or the shaft is movable between (i) a first position wherein the closure closes the at least one port to prevent passage of fluid through the at least one port and hermetically seal the at least one port with respect to ambient atmosphere, and (ii) a second position opening the at least one port to permit passage of fluid through the at least one port; and
        wherein the septum has an aperture therethrough configured to receive at least a portion of the shaft and the closure during said engaging of the first device and the second device; and
        wherein a portion of the closure radially adjacent to the port is adapted to at least partially penetrate into or through the aperture in the first position;
    penetrating the shaft and closure at least partially into or through the aperture;
    during or after the penetrating step, moving one or more of the closure or the shaft from the first position to the second position; and
    flowing fluid between the first device and the second device;
    wherein the penetrating step includes at least partially penetrating the closure into or through the aperture with the closure in the first position.

46. A method as defined in claim 45, wherein the septum is self-closing and the method further comprises, when the first and second devices are not engaged, substantially preventing one or more of fluid or contamination from passing or penetrating through the aperture.

47. A method as defined in claim 45, wherein the penetrating step includes one or more of (i) while the closure is in the first position, at least partially penetrating a portion of the closure extending along the at least one port in the first position into or through the aperture; (ii) substantially preventing any contact between the at least one port and the septum; or (iii) interposing the closure between the at least one port and septum.

48. A method as defined in claim 45, wherein the chamber is sealed with respect to ambient atmosphere, the penetrating step includes placing the second device in fluid communication with the chamber, and the flowing step includes flowing fluid from the second device to the chamber.

\* \* \* \* \*